United States Patent [19]
Crudele et al.

[11] Patent Number: 5,968,286
[45] Date of Patent: Oct. 19, 1999

[54] HEAT-MEDIATED CONDITIONING FROM SHAMPOO AND CONDITIONER HAIR CARE COMPOSITIONS CONTAINING SILICONE

[75] Inventors: Joanne Crudele, Chicago; Wolfgang Bergmann, Long Grove; Kimberly Kamis, Glenview; Pawel Milczarek; Varsha Shah, both of Schaumburg, all of Ill.

[73] Assignee: Helene Curtis, Inc., Chicago, Ill.

[21] Appl. No.: 08/943,610

[22] Filed: Oct. 3, 1997

[51] Int. Cl.$^6$ .............................. C11D 3/08; C11D 7/075; C11D 3/04
[52] U.S. Cl. ............................ 134/42; 510/392; 510/122; 510/137; 510/466; 424/70.11; 424/70.12
[58] Field of Search ............................. 424/70.11, 70.12; 510/122, 137, 466; 134/42

[56] References Cited

U.S. PATENT DOCUMENTS

| | | | |
|---|---|---|---|
| 4,704,272 | 11/1987 | Oh et al. ..................................... | 424/70 |
| 4,741,855 | 5/1988 | Grote et al. .............................. | 252/142 |
| 4,788,006 | 11/1988 | Bolich, Jr. et al. ...................... | 252/550 |
| 4,861,583 | 8/1989 | Sramek et al. ............................ | 424/70 |
| 5,034,218 | 7/1991 | Duvel et al. .............................. | 424/70 |
| 5,041,285 | 8/1991 | Lundmark et al. ....................... | 424/70 |
| 5,085,857 | 2/1992 | Reid et al. ................................ | 424/70 |
| 5,227,164 | 7/1993 | Lundmark et al. ...................... | 424/401 |
| 5,286,476 | 2/1994 | Nanba ....................................... | 424/47 |
| 5,362,486 | 11/1994 | Nandagiri et al. ........................ | 424/71 |
| 5,585,094 | 12/1996 | Villamarin ........................... | 424/70.12 |
| 5,622,694 | 4/1997 | Torgerson et al. . | |
| 5,639,448 | 6/1997 | Galleguillos et al. ............... | 424/70.11 |
| 5,730,966 | 3/1998 | Torgerson et al. .................. | 424/70.11 |
| 5,753,216 | 5/1998 | Leitch et al. ......................... | 424/70.16 |

FOREIGN PATENT DOCUMENTS

| | | |
|---|---|---|
| 2158538 | of 1997 | Canada . |
| 323739 | of 1989 | European Pat. Off. . |
| 0524346 | 1/1993 | European Pat. Off. . |
| 0694565 | 1/1996 | European Pat. Off. . |
| 87/289776 | of 1989 | Japan . |
| 87/308339 | of 1989 | Japan . |
| 87/328267 | of 1989 | Japan . |
| 89/04653 | 6/1989 | WIPO . |

OTHER PUBLICATIONS

Chart entitled: "Heat–Activated Conditioning of Hair Market Survey"—Moisturizing Shampoos.
Chart Entitled: "Heat–Activated Enhanced Conditioning Technology".
Ingredient Label—Revlon Outrageous Moisture Rich Dry Hair Shampoo—Lot #761.
Pantene Pro V Dry/Damaged Hair Shampoo—Lot#CV7083.
Pert Plus 2 in 1 Extra Moisturizing Conditioning Shampoo—Lot#BS7209.
Vidal Sassoon All–In–One Moisturizing Shampoo—Lot#AL7239.
Clairol Daily Defense 4 (Jan. 1998 Purchase Date).
Chart entitled: "Heat–Activated Conditioning of Hair Market Survey"—Moisturizing Conditioners.
Pantene Pro V Deep Conditioner—Lot#MN7139.
Vidal Sassoon Deep Conditioner—Lot#MW7079.
Revlon Outrageous Moisture Rich Dry Hair Conditioner—Lot#762.
L'Oreal Hydra Vive Moisturizing Conditioner (Jan. 1998 Purchase Date).
White Rain Nourishing conditioner (Jan. 1998 Purchase Date)—Not enclosed.
Clairol Daily Defense 4 Conditioner—Lot#11127A.

*Primary Examiner*—Kery Fries
*Attorney, Agent, or Firm*—Matthew Boxer

[57] ABSTRACT

This invention relates to a method for thermal conditioning of hair which comprises:

(a) applying to hair a rinse-off composition comprising:
  (1) a nonvolatile silicone conditioning agent; and
  (2) a carrier;
(b) rinsing the composition from the hair with water;
(c) applying heat via a heating appliance to the composition treated hair to dry or style the hair and wherein a reduction in the bending modulus caused by the silicone conditioning agent is at least 1.00%, and wherein the method of the invention results in the deposition on the hair of at least 30 ug silicone/1 g of hair.

11 Claims, No Drawings

HEAT-MEDIATED CONDITIONING FROM SHAMPOO AND CONDITIONER HAIR CARE COMPOSITIONS CONTAINING SILICONE

BACKGROUND OF INVENTION AND PRIOR ART

There is sufficient evidence both from both consumer and clinical testing that the use of heat styling appliances is damaging to human hair.

For consumers that heat style, their primary concern is to use a shampoo or conditioner treatment that can protect and improve the condition of their hair. Shampoos and conditioners containing silicone conditioning agents are able to deliver these benefits by 1)coating the hair with a conforming layer of silicone that smoothes the hair's imperfections such as roughness, cracks, cuticle uplift, or cuticle removal, and, 2) helping to protect the hair from extreme internal water loss with heat. As a result of coating the hair with conditioning agents, shampoo and conditioner treatments often impart increased softness, better combing characteristics, luster, and in general, improve the appearance of one's hair.

The claimed invention not only protects the hair from the damaging action of heat, but in addition, uses heat to mediate increased conditioning or softness dependent on the delivery and deposition of conditioning agent between certain known levels.

SUMMARY OF THE INVENTION

The invention is the use of silicone based conditioning agents in shampoos, conditioners or the like, to elicit a heat-mediated reduction in bending modulus, or softening, or conditioning to hair, as compared to air dried, treated hair. The heat required to elicit the effect would be the heat exposure of a blow dryer or styling appliance, measured at point of origin of the appliance to be typically between 200° F. to 400° F.

In brief, the present invention is directed to a method for thermal conditioning hair which comprises:

(a) applying to hair a rinse-off composition comprising:
  (1) a nonvolatile, silicone conditioning agent; and
  (2) a carrier;
(b) rinsing the composition from the hair with water;
(c) applying heat via a heating appliance to the composition treated hair to dry or style the hair and wherein a reduction in the bending modulus caused by the silicone conditioning agent is at least 1.00%, and wherein the method of the invention results in the deposition on the hair of at least 30 ug silicone/1 g of hair.

DETAILED DESCRIPTION OF THE INVENTION

As used herein nonvolatile, silicone conditioning agent means any silicone having a boiling point of 200° C. or greater, typically this would include silicones within a broad range of molecular weight, and having viscosities of between about 5 centistokes to 1 million centistokes.

As used herein, SLES means sodium lauryl ether sulfate.

As used herein, heating device means heating appliance.

As used herein, % means weight % unless otherwise indicated.

Heat activation is defined as some change that is mediated by use of the composition of the invention with heat, from styling appliances such as a blow dryer, curling iron, hot curler, hot brush, hot comb, hot rollers, crimper, or hair dryer. From internal testing of various appliances this average temperature can range on the "hot" setting to be 2000 to 400° F.

Any nonvolatile silicone conditioning agent which will deposit silicone on hair may be used in the compositions and methods of the present invention. Silicone agents in the compositions of the present invention include dimethicone, dimethiconol, phenyl trimethicone, dimethicone copolyols, amino functional silicones, organically modified silicone resins such as stearyl siloxysilicate and lauric siloxysilicate, silicone gums, silicone elastomers, and crosslinked siloxane polymers which may be either linear or branched.

Silicone conditioning agents are responsible for a heat-induced reduction in bending modulus or softening of the hair. The preferred non-volatile silicone conditioning agents are dimethiconol, dimethicone, amodimethicone which are added to a composition of the present invention in an amount sufficient to provide improved combing and improved feel (softness) to the hair after shampooing.

Preferred silicones include linear and branched polydimethylsiloxanes, of the following general formula: $(CH_3)_3\ SiO-[Si(CH_3)_2O]_n-Si(CH_3)_3$, wherein n is from about 7 to about 15,000, preferably from about 7 to about 9,000. Silicones useful in compositions of the present invention are available from a variety of commercial sources, including General Electric Company and Dow Corning. In addition to the linear and branched polydimethylsiloxanes, the polydimethylsiloxanes can be organically modified to include amine, hydroxyl, alkyl, alkyl aryl, ethoxylated, and propoxylated functionalities.

In accordance with one important embodiment, the composition of the present invention also includes from about 0.1% to about 10%, particularly about 0.5% to about 10%, and preferably from about 1.0% to about 5.0%, by weight of a non-volatile silicone compound or other conditioning agent(s), preferably a water-insoluble, emulsifiable conditioning agent. Any nonvolatile silicone agent will work in the compositions and methods of the invention provided that the silicone agent deposits silicone onto the hair.

Using compositions and methods of the invention, wherein the nonvolatile, silicone conditioning agent was present in the compositions at an active range of about 0.1 to about 2.0%, depositing on hair in the range of about 30 ug/g to about 1200 ug/g hair. In these just above mentioned compositions, the nonvolatile, silicone conditioning agents were as follows:

Dimethiconol containing silicone emulsions such as, Dimethiconol (and) TEA-Dodecylbenzenesulfonate (and) Polyethylene Oxide Laurel Ether. Non-emulsion forms of silicone conditioning agents include dimethicone; and amodimethicone.

The surface active agent can be anionic, cationic, nonionic, zwitterionic or amphoteric. Typically useful surface active agents contain at least one fatty, carbon atom, chain. The individual surface active agents can also be used in mixtures of two or more surface active agents or their salts.

Exemplary anionic surface active agents include but are not limited to alkali metal and ammonium salts of fatty alkyl sulfates and fatty alpha-olefin sulfonates such as ammonium lauryl sulfate and the sodium alpha-olefin sulfonate prepared from mixed olefins having about 12 to 18 carbon atoms in the fatty chain, alkali metal and ammonium soaps such as potassium oleate and ammonium palmitate, alkali metal ethoxylated fatty alkanol sulfates and phosphates such as sodium polyoxyethylene myristyl sulfate and potassium polyoxyethylene lauryl phosphate in which there are an average of 1 to about 4 oxyethylene units per molecule, and the like.

Exemplary nonionic surface active agents include but are not limited to polyoxyethylene derivatives of fatty alcohols containing about 4 to about 25 oxyethylene units per molecule such as polyoxyethylene (20) cetyl ether and polyoxyethylene (4) lauryl ether, polyoxyethylene derivatives of octyl- and nonylphenols containing an average of about 4 to about 25 oxyethylene units such as polyoxyethylene (9) octylphenyl ether and polyoxyethylene (15) nonylphenyl ether, mono- and dialkanol amides of fatty acids such as N-(2-hydroxyethyl) tallow acid amide and N,N-bis-(2-hydroxyethyl) coco fatty acid amide, and the like.

Exemplary cationic surface active agents include but are not limited to quaternary nitrogen-containing compounds that include the following structures: (1) one fatty chain and three lower alkyl (one to four carbon atoms) substituents on the quaternary nitrogen such as stearyltrimethylammonium chloride and cetyldimethylethylammonium bromide; (2) one fatty chain, two lower alkyl groups and a benzyl group such as cetyldimethylbenzylammonium bromide; (3) two fatty chains and two lower alkyl groups such as dimethyldi-(hydrogenated tallow)-ammonium chloride; (4) three fatty chains and one lower alkyl group such as tricetylmethylammonium chloride; and the like.

Exemplary zwitterionic surface active agents include but are not limited to betaine and sultaine derivatives such as stearyldimethylglycine, cocamidopropyidimethylglycine, cocamidopropyidimethyl sultaine, cocamidopropylbetaine and the like, as well as fatty tertiary amine oxides such as dimethylcocoamine oxide and dimethylstearylamine oxide.

Illustrative amphoteric surface active agents include but are not limited to fatty chain derivatives of mono- and dicarboxy substituted imidazolines such as 2-heptadecyl-1-carboxymethyl-1-(2-hydroxyethyl)-2-imidazolinium chloride, 2-undecyl-1-(sodium carboxymethyl)-1-(2-hydroxyethyl)-2-imidazolinium hydroxide. Also included among the amphoteric surface active agents are fatty derivatives of glycine such as lauryl aminopropylglycine.

The word "fatty" is used herein to refer to carbon atom chains that contain about 12 to about 18 carbon atoms. The word "fatty" is also used in conjunction with carbon atom chains that are derived from chains of about 12 to about 18 carbon atoms, wherein at least one atom of the chain is within a ring structure, rather than being pendant from that ring structure, as is the case for one imidazoline derivative discussed hereinbefore.

The composition also can include a suspending agent for the conditioning agent, in an amount of about 0.5% to about 10%, by total weight of the composition. The particular suspending agent is not critical and can be selected from any materials known to suspend water-insoluble liquids in shampoo or conditioner compositions. Suitable suspending agents are for example, distearyl amate (distearyl phthalamic acid); fatty acid alkanolamides; esters of polyols and sugars; polyethyleneglycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic alkanolamide also is optionally included in an amount of about 0.1% to about 5% by weight in the shampoo or conditioner compositions that include a conditioning agent to provide exceptionally stable emulsification of water-insoluble conditioning agents and to aid in thickening and foam stability.

Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh et al. U.S. Pat. No. 4,704,272 Grote et al. U.S. Pat. No. 4,741,855; and Bolich, Jr. et al. U.S. Pat. No. 4,788,006, which patents are hereby incorporated by reference.

Other useful suspending and thickening agents can be used instead of the alkanolamides such as monosodium glutamate, sodium alginate; guar gum; xanthan gum; gum arabic; cellulose derivatives, such as carbomer, methylcellulose, hydroxybutylcellulose, hydroxyethylcellulose, hydroxypropylcellulose and carboxymethylcellulose; and various synthetic polymeric thickeners, such as the polyacrylic acid derivatives.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS(R). When present, such stabilizers comprise from about 0.05% to about 1%, preferably from about 0.1% to about 0.8%, by weight of the composition.

Other common cosmetic additives can be incorporated with the essential ingredients of the present invention, as long as the basic properties of the shampoo and conditioners or the like are not adversely affected. These additives include, but are not limited to, commonly used fragrances, dyes, opacifiers, pearlescing agents, foam stabilizers, preservatives, water softening agents, acids, bases, sequestering agents, buffers, protein, amino acids, other non-silicone conditioning agents and the like; and will usually be present in weight percentages of less than about 1%each, and about 2% to about 5% in total.

The composition vehicle, or carrier, is predominantly water but organic solvents also can be added to the composition in order to solubilize compounds that are not sufficiently soluble in water. Suitable solvents include the lower alcohols like ethanol and isopropanol; polyols like glycerol; glycols or glycol ethers, like 2-butoxyethanol, ethylene glycol, ethylene glycol monoethyl ether, propylene glycol and diethylene glycol monomethyl ether; and mixtures thereof. These solvents can be present in the shampoo or conditioner or the like composition of the present invention in an amount from about 1% to about 85% by weight and, in particular, from about 5% to about 50% by weight, relative to the total weight of the composition.

Hair serums are included within the compositions of the invention.

FORMULATION EXAMPLES

As shown in the data below, nonvolatile silicone conditioning agents, contained within the formulations of the invention and depositing silicone within certain ranges, are responsible for the heat-mediated reduction in bending modulus, or hair softening, or conditioning.

Shampoo formulations were tested for heat induced bending modulus changes. The formulas ranged from base shampoo detergent in water, next, to the addition of carbopol, propylene glycol, jaguar, and anionic silicone emulsion (DC1784), to base detergent and water with DC1 784. The shampoo formulations and results are presented in Table I. Only hair arrays treated with the formulas of the invention containing silicone with jaguar(D, F) and silicone alone (E) exhibit any statistical change in modulus, a reduction of approximately 8.00%, 6.00%, and 7.00%, respectively.

TABLE I

SHAMPOO COMPOSITIONS, INGREDIENTS, WT %, AND BENDING MODULUS RESULT($P > .05$)

| SHAMPOO FORMULATION | INGREDIENTS | WT % | BENDING MODULUS |
|---|---|---|---|
| Formula A | SLES -2 moles | 56.00 | No change |
|  | Cocamidopropyl Betaine | 6.7 |  |
|  | Water | q.s.* |  |
| Formula B | SLES -2 moles | 56.00 | No Change |
|  | Cocamidopropyl Betaine | 6.7 |  |
|  | Carbopol Slurry[1] | 20.00 |  |
|  | Water | q.s. |  |
| Formula C | SLES -2 moles | 56.00 | No Change |
|  | Cocamidopropyl Betaine | 6.7 |  |
|  | Carbopol Slurry | 20.00 |  |
|  | Jaguar[2] | 0.1 |  |
|  | Propylene Glycol | 0.5 |  |
|  | Water | q.s. |  |
| Formula D | SLES -2 moles | 56.00 | Approximate |
|  | Cocamidopropyl Betaine | 6.7 | Reduction of |
|  | Carbopol Slurry | 20.00 | 8.00% |
|  | Jaguar | 0.1 |  |
|  | Propylene Glycol | 0.5 |  |
|  | Dimethiconol (DC1784) | 4.0 |  |
|  | Water | q.s. |  |
| Formula E | SLES -2 moles | 56.00 | Approximate |
|  | Cocamidopropyl Betaine | 6.7 | Reduction of |
|  | Carbopol Slurry | 20.00 | 7.00% |
|  | Dimethiconol (DC1784) | 4.0 |  |
|  | Water | q.s. |  |
| FORMULA F | SLES -2 moles | 56.00 | Approximate |
|  | Cocamidopropyl Betaine | 6.7 | Reduction of |
|  | Carbopol Slurry | 20.00 | 6.00 |
|  | Jaguar | 0.1 |  |
|  | Propylene Glycol | 0.5 |  |
|  | Dimethiconol (DC1784) | 1.5 |  |
|  | Water | q.s. |  |

*q.s. - quantity sufficient for the formula weight percentage to equal 100%.
[1]2% Carbomer slurry
[2]Jaguar is guar-hydroxypropyltrimmonium chloride Conditioner formulations were tested for heat induced bending modulus changes. The compositions and bending modulus results are listed in Table II.

TABLE II

CONDITIONER COMPOSITIONS, INGREDIENTS, WT %, AND BENDING MODULUS RESULT($P > .05$)

| CONDITIONER G INGREDIENTS | INGREDIENTS | BENDING MODULUS RESULT |
|---|---|---|
| water, soft | q.s.* | Reduction of 4.00% |
| cetrimonium chloride | 4.65 |  |
| cetyl/stearyl alcohol | 3.75 |  |
| cetyl alcohol | 3.75 |  |
| paraffin wax | 1.25 |  |
| stearyl stearate | 0.50 |  |
| dimethiconol (DC 1784) | 2.50 |  |
| fragrance/preservatives | 0.90 |  |

| CONDITIONER H INGREDIENTS | WEIGHT % | BENDING MODULUS RESULT |
|---|---|---|
| water, soft | q.s.* | Approximate Reduction of 5.00% |
| natrosol (250 HHR) | 0.2500000 |  |
| stearylamidopropyl dimethylamine | 0.5000000 |  |
| liquid citric acid 50% | 0.1850000 |  |
| stearyl octyldimonium methosulfate | 1.7500000 |  |
| cetyl alcohol | 2.7500000 |  |
| stearyl alcohol | 1.2500000 |  |
| behenamidopropyl ethyldimonium ethosulfate | 0.7200000 |  |
| preservatives | 0.2800000 |  |
| amodimethicone (DC929) | 1.2500000 |  |
| cyclomethicone | 1.6000000 |  |
| fragrance | 0.6000000 |  |
| ajidew (N-50) | 0.0200000 |  |
| glycerin USP | 0.0500000 |  |
| solu-soy (EN-25) | 0.0450000 |  |
| potassium hydroxide (liquid 50%) | 0.1000000 |  |

| CONDITIONER I INGREDIENTS | WEIGHT % | BENDING MODULUS RESULT |
|---|---|---|
| water, soft | q.s. | Approximate Reduction of 3.00% |
| propylene glycol | 0.5000000 |  |
| stearylamidopropyl dimethyl amine | 0.5000000 |  |
| liquid citric acid (50% liquid) | 0.1850000 |  |
| dicetyldimonium chloride | 2.1000000 |  |
| cetyl alcohol | 3.7500000 |  |
| stearyl alcohol | 1.0000000 |  |
| disodium EDTA | 0.1000000 |  |
| preservative | 0.1800000 |  |
| dimethicone | 0.1000000 |  |
| cyclomethicone | 1.8000000 |  |
| fragrance | 0.6000000 |  |

*q.s. - quantity sufficient for the total formula weight percentage to equal 100%.

TESTING METHOD
Dynamic Mechanical Testing of Bending Modulus

Dynamic mechanical testing of the force or modulus to bend a bundle of hair fibers characterizes the stiffness of the hair array, i.e., its resistance to a controlled normal force imposed on the array in the vertical direction. If the modulus increases with treatment the array is stiffer. If the modulus decreases with treatment the array is less stiff; softer; fibers have reduced interfiber friction.

The measurement of bending modulus is not unique to analysis of the physical properties of hair, but reported works had been exclusively devoted to the properties of single hair fiber (see Robbins, Clarence R., Chemical and Physical Behavior of Hair, Third edition. Springer-Verlag, N.Y. 1993 herein incorporated by reference) and therefore never addressed the characteristics of multiple fibers. In addition, the bending modulus was calculated from the deflection of a single fiber in a static not dynamic mode as used in this test method and reported in the literature for other materials (Lee, T. H., Boey, F. Y., and Loh, N. L. Characterization of Fibre-Reinforced PPS Composite By Dynamic Mechanical Analysis: Effect of Aspect Ratio and Static Stress. *Composites Science and Technology* 49 (1993) 217–223).

Instruments are commercially available to measure the mechanical properties of a variety of materials, hair included. The Perkin Elmer DMA 7 Dynamic Mechanical Analyzer, used at Helene Curtis R & D, is equipped to perform three point bending modulus, and was used for thermal studies of bending modulus of treated hair. The use of a hair bundle or array allows evaluation of multiple fiber changes and/or fiber interaction in contrast to single fiber effect.

Two hundred fifty fibers of the same length are selected from a regular brown hair tress. The fibers are wetted and aligned on a flat surface to form a ribbon-like swatch. A single drop of water proof adhesive is placed at five spots on the swatch. The distance between each junction is about 1 inch. When dry, four bundles are cut from one swatch.

Eight hair bundles are treated with a composition per treatment group. The weight of each hair bundle is measured prior to the test in order to assure that the amount of composition applied remains at a constant proportion to the mass of hair of 1:10 for shampoos and 3:5 with respect to conditioners. For rinse-off products such as shampoos and conditioners, the desired amount of product is applied with a micropipette to the wet hair, worked in for 30 seconds and rinsed out in warm water for 30 seconds. All samples are air dried in the instrument at 72F and a controlled humidity of 30%. To heat the sample in the testing chamber the DMA furnace is engaged to 200° F., and the sample is heated for approximately 7 minutes.

Bending Modulus Results: Thermally-induced Changes to the Bending Modulus of Formulas of the Invention-Treated Hair Arrays.

The results of testing are presented in Tables I and II. Hair arrays treated with the shampoo and conditioner formulations of the invention, exhibit a statistically significant reduction in bending modulus ($p<0.05$), following heat treatment. Measurement of the storage bending modulus of untreated, air dried hair vs. heated hair reveals that untreated hair will exhibit an increase in bending modulus of approximately +8.00%, probably due to water loss. All decreases in bending modulus listed in Tables I and 11 are statistically significant at >95% confidence level using a t-test to compare the means of the treated air-dried samples vs. treated, heated samples.

What is claimed is:

1. A method for thermal conditioning hair which comprises:
   (a) applying to hair a rinse-off composition comprising:
      (1) a nonvolatile, silicone conditioning agent; and
      (2) a carrier;
   (b) rinsing the composition from the hair with water;
   (c) applying heat via a heating appliance to the composition treated hair to dry or style the hair and wherein the heated silicone conditioning agent causes a reduction in the bending modulus of at least 1%.

2. A method according to claim 1, wherein the silicone conditioning agent is any silicone having a boiling point of 200° C. or greater.

3. A method according to claim 1, wherein the nonvolatile, silicone conditioning agent is in an emulsion.

4. A method according to claim 1, wherein the nonvolatile, silicone conditioning agent is selected from the group consisting of dimethicone, dimethiconol, phenyl trimethicone, dimethicone copolyols, amino functional silicones, organically modified silicone resins such as stearyl siloxysilicate and lauric siloxysilicate, silicone gums, silicone elastomers, and crosslinked siloxane polymers which may be either linear or branched.

5. A method according to claim 1, wherein the heating appliance or device is a blow-dryer, curling iron, hot comb, hot curlers, hot rollers, hot brush, crimper, or hair dryer.

6. A method according to claim 1, wherein temperature of the heating appliance during the heating step is from about 200° F. to about 400° F.

7. A method according to claim 1, wherein the composition is a hair serum.

8. A method according to claim 1, wherein the hair being conditioned is in a hairpiece, extension, or wig.

9. A method for thermal conditioning hair which comprises:
   (a) applying to hair a rinse-off composition comprising:
      (1) a nonvolatile, silicone conditioning agent; and
      (2) a carrier;
   (b) rinsing the composition from the hair with water;
   (c) applying heat via a heating appliance to the composition treated hair to dry or style the hair and wherein the heated silicone conditioning agent causes a reduction in the bending modulus of at least 1%, and wherein the method of the invention results in the deposition on the hair of at least 30 ug silicone/1 g of hair.

10. A method for conditioning hair according to claim 1 wherein the reduction in the bending modulus caused by the silicone conditioning agent is at least 2.00%.

11. A method for thermal conditioning hair according to claim 1 wherein the amount of silicon deposited on the hair is at least 60 ug silicone/1 g of hair.

* * * * *